United States Patent [19]

Kang et al.

[11] Patent Number: 4,529,796
[45] Date of Patent: Jul. 16, 1985

[54] METHOD FOR MAKING CHROMOGENIC AND/OR FLUOROGENIC SUBSTRATES FOR USE IN MONITORING CATALYTIC OR ENZYMATIC ACTIVITY

[75] Inventors: Jemo Kang, Skillman, N.J.; Glen L. Tolman, Chelmsford, Mass.

[73] Assignee: Baker Instruments Corporation, Allentown, Pa.

[21] Appl. No.: 349,577

[22] Filed: Feb. 22, 1982

Related U.S. Application Data

[63] Continuation-in-part of Ser. No. 248,682, Mar. 30, 1981, abandoned.

[51] Int. Cl.³ ............................................. C07H 15/12
[52] U.S. Cl. ....................................... 536/29; 536/27; 536/28
[58] Field of Search ............................... 536/29, 27, 28

[56] References Cited

U.S. PATENT DOCUMENTS

| | | | |
|---|---|---|---|
| 4,266,048 | 5/1981 | Horwitz et al. | 536/27 |
| 4,378,458 | 3/1983 | Gohlke et al. | 536/27 |

FOREIGN PATENT DOCUMENTS

| | | | |
|---|---|---|---|
| 17-11078 | 6/1942 | Japan | 536/27 |
| 47-11752 | 4/1972 | Japan | 536/29 |
| 5132572 | 9/1974 | Japan | 536/29 |
| 1170933 | 11/1969 | United Kingdom | 536/27 |

OTHER PUBLICATIONS

Smrt and S. Chladek, Czech. Chem. Commun., vol. 31, 1966, pp. 2978–2984.
Kole and Sierakowska, Acta Biochim. Polonica, vol. 18, No. 2, pp. 187–197, (1971).

Primary Examiner—Ethel G. Love
Attorney, Agent, or Firm—George W. Rauchfuss, Jr.

[57] ABSTRACT

A method for preparing a substrate capable of undergoing catalytic-induced hydrolysis of the phosphate ester at the 3' position, to yield a species capable of being monitored spectrophotometrically or fluorometrically, comprises (a) forming a mononucleotide 20', 3' cyclic phosphate of the formula:

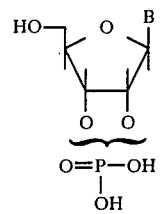

wherein B is a nucleotide base, and wherein the CH₂OH group at the 4'-position is either cis or trans to the cyclic phosphate;

(b) blocking said mononucleotide 2', 3'-cyclic phosphate at the 5'-hydroxyl with a suitable 5'-blocking member to form a mononucleotide 5'-O-blocked-2', 3'-cyclic phosphate;

(c) opening said cyclic phosphate so that essentially only a mononucleotide 5'-O-blocked-2'-hydroxyl-3'-phosphate is formed under conditions leaving the 5'-position essentially blocked;

(d) blocking said mononucleotide 5'-O-blocked 3'-phosphate at the 2'-hydroxyl with a suitable 2'-O-blocking member to form a mononucleotide 2'-blocked-5'-blocked-3'-phosphate; and (e) forming a 2'-O-blocked-5'-O-blocked phosphodiester by bonding said mononucleotide 2'-O-blocked-5'-O-blocked-3'-phosphate with a moiety selected from the group consisting of a chromophore or fluorophore.

The 2'-blocking member is removed from said 2'-blocked-5'-blocked phosphodiester so as to provide a substrate characterized by the ability to undergo catalytic-induced hydrolysis of the phosphodiester to yield a species capable of being monitored spectrophotometrically or fluorometrically.

31 Claims, No Drawings

METHOD FOR MAKING CHROMOGENIC AND/OR FLUOROGENIC SUBSTRATES FOR USE IN MONITORING CATALYTIC OR ENZYMATIC ACTIVITY

This application is a continuation-in-part of our earlier application Ser. No. 248,682 filed Mar. 30, 1981, now abandoned.

RELATED APPLICATIONS

Farina and Gohlke, Ser. No. 248,689 filed Mar. 30, 1981, now U.S. Pat. No. 4,378,428 issued Mar. 29, 1983, for A Method for Carrying Out Non-Isotopic Immunoassays, Labeled Analytes and Kits for Use in Such Assays.

Gohlke, Hedaya, Kang and Mier, Ser. No. 248,672 filed Mar. 30, 1981, now U.S. Pat. No. 4,378,458 issued Mar. 29, 1983, for Novel Chromogenic and/or Fluorogenic Substrates for Monitoring Catalytic or Enzymatic Activity.

Kang, Ser. No. 248,688 filed Mar. 30, 1981, now abandoned, for a Method of Making Chromogenic and/or Fluorogenic Substrates for Use in Monitoring Catalytic or Enzymatic Activity.

BACKGROUND OF THE INVENTION

1. Field of the Invention

The present invention relates to chromogenic and/or fluorogenic mononucleotide-3'-phosphodiesters, and, more particularly, to a novel method for synthesizing such mononucleotide phosphodiesters. These materials may be used, for example, in carrying out various non-isotopic immunoassays.

2. Description of the Prior Art

For a variety of clinical purposes such as, for example, monitoring dosage schedules, monitoring hormone levels, checking for recent ingestion or following pharmacological dynamics of bioavailability, absorption, degradation or excretion, it is a great advantage to measure the concentration of various drugs or the like to the nanomolar or even picomolar level. As is known, radioimmunoassay can accomplish analyses of this type. To carry out an analysis, an acceptable kit or system must include an antiserum, a standard of the compound (i.e., —analyte) to be measured, the radiolabeled derivative of the compound to be measured, a buffering agent or agents and, often, a displacing agent. The antiserum is produced by bleeding animals which have been immunized by innoculation, for example, with the hapten-protein conjugate (immunogen) corresponding to the compound to be measured.

As is well known, in general, the technique of radioimmunoassay measures the competition between radioactively labeled analyte and unlabeled analyte for binding sites on the antibody in the antiserum. By adding to the antiserum known amounts of the analytes to be assayed and a radiolabeled analog, a dose-response curve for bound or free analyte versus concentration of analyte is constructed. After this immunocalibration has been carried out, unknown concentrations can then be compared to the standard dose-response curve for assay. Crucial to this type of assay is the existence of radioactive analytes which compete effectively with non-radioactive analytes. Accordingly, in order to obtain the maximum precision, accuracy, sensitivity, specificity and reproducibility of the assay, purified, well-characterized synthetic radioactive analytes are required.

Several deficiencies in radioimmunoassay methodology have been identified. First of all, it is necessary to make a physical separation of the antibody bound radiolabeled analyte from the free radiolabeled analyte. Further, the methodology is considered rather labor intensive, and the equipment required is likewise relatively expensive, is not uniformly available, and further requires the use of highly trained and skilled technicians to accurately carry out such assays. Likewise, the radioisotopically-labeled analytes are relatively unstable and expensive and pose an increasingly severe waste disposal problem owing to radiation exposure hazards associated with the commonly used radioisotopic labels. Despite these shortcomings, the use of radioimmunoassay has grown considerably.

The substantial recent growth in the use of radioimmunoassay in clinical laboratories has, however, spurred the development of variants which overcome the deficiencies of the radioimmunoassay methodology as described herein. The approaches which have been developed to overcome these deficiencies primarily involve the use of enzyme or fluorescent labels instead of radioisotopic labels, preferably coupled with conditions allowing for measuring a chemical distinction between bound and free fractions of labeled analyte which leads to the elimination of the requirement for physical separation. Immunoassays having the latter simplifing and advantageous feature are referred to as homogeneous immunoassays as opposed to heterogeneous immunoassays where physical separation is required.

Thus, homogeneous immunoassay systems have been developed which are based on the use of an enzyme-labeled analyte where the enzymatic activity of the label is decreased when complexation with the antibody occurs. Unlabeled analyte whose concentration is to be determined displaces the enzyme-labeled analyte bound to the antibody, thus causing an increase in enzymatic activity. Standard displacement or dose-response curves are constructed where increased enzymatic activity (monitored spectophotometrically using what has been termed a "substrate" which ultimately produces a unique chromophore as a consequence of enzyme action) is plotted against increased analyte concentration. These are then used for determining unknown analyte concentrates. The following U.S. patents have been issued in the field of homogeneous enzyme immunoassay: U.S. Pat. Nos. 3,817,837; 3,852,157; 3,875,011; 3,966,556; 3,905,871; 4,065,354; 4,043,872; 4,040,907; 4,039,385; 4,046,636; 4,067,774; 4,191,613; and 4,171,244. In these patents, the label for the analyte is described as an enzyme having a molecular weight substantially greater than 5,000. Also, commercialization of this technology has been limited so far to applications where the analytes are relatively small in molecular size at fluid concentrations of the analyte greater than $10^{-10}M$.

As a consequence of the limitations of the homogeneous enzyme immunoassay technique described above, considerable effort has been devoted towards developing more sensitive homogeneous immunoassays using fluorescence. These have been primarily directed at assays for the larger sized molecules such as immunoglobulins or polypeptide hormones such as insulin. The following U.S. patents have been issued for this type of assay: U.S. Pat. Nos. 3,998,943; 3,996,345; 4,174,384;

4,161,515; 4,208,479 and 4,160,016. The label in most of these patents involves an aromatic fluorescent molecule, bound either to the analyte or to the antibody. All likewise involve various methods of quenching fluorescence through antibodies or other fluorescent quenchers so that the extent of quenching is related to the amount of analyte present in the sample.

A further type of methodology which may be described as a reactant-labeled fluorescent immunoassay involves the use of a fluorescent-labeled analyte designed so that a fluorescent product is released when it is enzymatically hydrolyzed. Antibody to the analyte portion of the molecule, however, inhibits enzymatic hydrolysis. Consequently, by the law of mass action, fluorescence is enhanced in the presence of increased analyte due to enzymatic hydrolysis of the displaced, fluorescent labeled analyte. As an example, a labeled analyte is β-galactosyl-umbelliferone-sisomicin. The enzyme β-galactosidase cleaves the sugar from the umbelliferone moiety which can then fluoresce. Publications which describe this methodology include: J. F. Burd, R. C. Wong, J. E. Feeney, R. J. Carrico and R. C. Boguolaski, *Clin. Chem.*, 23, 1402(1977); Burd, Carrico, M. C. Fetter, et al., *Anal. Biochem.*, 77, 56 (1977) and F. Kohen, Z. Hollander and Boguolaski, *Jour. of Steroid Biochem.*, 11, 161 (1979).

The previously identified co-pending Farina et al. application provides methodology for carrying out non-isotopic immunoassays which obviates the deficiencies of prior assays of this general type. In an illustrative embodiment, this methodology utilizes a labeled analyte-polypeptide complex which expresses ribonuclease-type activity to catalytically convert a substrate to a chromogenic or fluorogenic reporter molecule.

Many organic compounds have been utilized heretofore for monitoring the catalytic activity of ribonuclease. Such organic compounds, or substrates, as they are commonly referred to, include ribonucleic acid itself, cyclic phosphate diesters, and monoribonucleotide compounds which exhibit the same or similar structural constraints as those expressed by the natural substrate.

Thus, for example, one method for monitoring the catalytic activity of ribonuclease involves the use of a ribonucleic acid solution. That method involves monitoring a decrease in absorbance at 300 nm of a ribonucleic acid solution as a function of time, M. Kunitz, *J. Biol. Chem.*, 164, 563 (1946). Although that method is relatively simple to conduct, it has several deficiencies; specifically, the rate of decrease of absorption is not linear, calibration of each substate solution is required, and direct monitoring of absorbance decreases at 300 nm is impractical with clinical samples.

Another method utilized for monitoring ribonuclease activity is an end-point variant of the procedure described above. In the end point variant procedure, yeast ribonucleic acid is incubated with the enzyme sample for a fixed period of time. The remaining RNA is precipitated with perchloric acid or uranyl acetate/trifluoroacetic acid, and the absorbance of the supernatant is measured after centrifugation. S. B. Anfinsen, R. R. Redfield, W. L. Choate, A. Page, and W. R. Carroll, *Jour. Biol. Chem.*, 207, 201 (1954). However, that method is much too cumbersome for homogeneous immunoassays of the type described in the co-pending Farina et al. application, primarily due to the precipitation step involved.

Yet another variation of the above procedures has been reported by R. C. Kamm, A. G. Smith, and H. Lyons, *Analyt. Biochem*, 37, 333 (1970). The method described therein is based on the formation of a fluorescent reaction product resulting from the reaction of the dye ethidium bromide with intact yeast ribonucleic acid, but not with the hydrolysis products. In that method, a fluorescent signal, which is monitored, decreases with time. However, monitoring a fluorescent signal which decreases with time is disadvantageous, as the method may result in a lack of sensitivity when only modest differences in enzyme concentration are encountered. In addition, other disadvantages are that the rate of decrease of absorption is not linear, and calibration of each substrate solution is required.

Another known substrate for monitoring ribonuclease activity is a mononucleotide substrate, cytidine 2′, 3′-phosphate diester, E. M. Crook, A. P. Mathias, and B. R. Rabin, *Biochem. J.*, 74, 234 (1960). In that method, an increase of absorbance at 286 nm, corresponding to the hydrolysis of the cyclic phosphate ring, is monitored over a two-hour period to measure the ribonuclease activity of the sample. This method, however, cannot be used in homogeneous immunoassay methods of the type described in the Farina et al. co-pending application because there are analyte sample interferences which occur at 286 nm. Furthermore, the distinction between the substrate and product absorbance spectra is small, with the ratio of extinction coefficients being only 1.495 at 286 nm.

Further, certain mononucleotide-3′-phosphodiesters, including, 1-naphthyl esters of 3′-uridylic, 3′-inosonic and 3′-adenylic acids have been utilized as ribonuclease substrates. These napthyl esters have been used to differentiate substrate specificities of ribonucleases from various sources. H. Sierakowska, M. Zan-Kowalczewska, and D. Shugar, *Biochem. Biophys. Res. Comm.*, 19, 138 (1965); M. Zan-Kowalczewska, A. Sierakowska, and D. Shugar, *Acta. Biochem. Polon.*, 13, 237 (1966); H. Sierakowska and D. Shugar, *Acta. Biochem. Polon.*, 18, 143 (1971); H. Sierakowska, H. Szemplinska, D. Shugar, *Biochem. Biophys. Res. Comm.* 11, 70 (1963). As a result of ribonuclease-induced hydrolysis, the use of such substances results in the liberation of 1-naphthol which is allowed to react with a diazonium salt to form an azo compound having strong visible absorbance. This approach requires that the assay kit include a separately packaged dye former (viz. - a diazonium salt). Also, this substrate cannot be employed in a fluorometric mode.

Various syntheses have been developed heretofore for the preparation of mononucleotide-3′-phosphodiesters. One such method for the preparation of uridine-3′-(1-naphthyl) phosphate is that disclosed in R. Kole and H. Sierakowska, *Acta Biochim. Polon*, 18, 187 (1971). In accordance with the method shown therein, uridine is acetylated at the 3′-hydroxyl position:

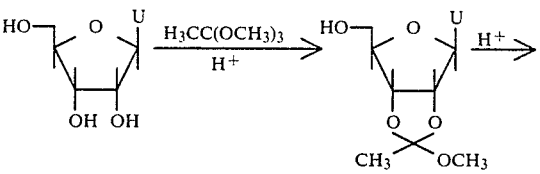

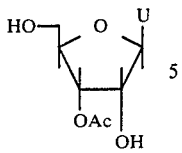

Next the 2'- and 5'-hydroxyl groups of 3'-O-acetyluridine are blocked with dihydropyran; and sequentially the 3'-O-acetyl undergoes hydrolysis so that 2',5'-bis-O-(tetrahydropyranyl) uridine is formed:

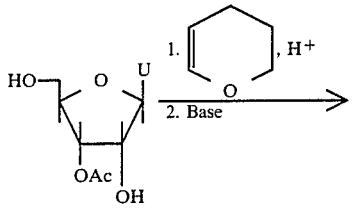

Condensation of 2',5'-bis-O-(tetrahydropyranyl)uridine with naphthyl phosphate/dicyclohexylcarbodiimide or naphthyl phosphoryldichloride then results in 1-naphthyl phosphorylation of the 3'-hydroxyl to form the blocked form of the substrate 2',5'-di-O-(tetrahydropyranyl) uridine-3'-(1-naphthyl) phosphate:

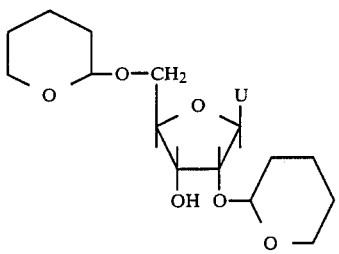

The tetrahydropyranyl blocking groups are acid labile and may be removed without competitive phosphate hydrolysis to form the substrate, uridine-3'-(1-naphthyl) phosphate:

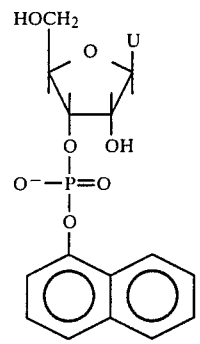

A variation of the synthesis described in Sierakowska and Shugar discussed above, is the method described in Rubsamen, Khandler and Witzel (Hoppe-Seyler's) Z. Physiol. Chem., 355, 687 (1974). There, uridine-2',5'-bis-O-(tetrahydropyranyl)-3'-phosphate is prepared by the reaction of dihydropyran with uridine-3'-phosphate. Dephosphorylation of the 2',5'-bis-O-(tetrahydropyranyl)-3'-uridine phosphate with, for example, phosphatase or lead (II) hydroxide, forms 2',5'-di-O-(tetrahydropyranyl) uridine. The 3'-hydroxyl of that compound may then be phosphorylated in the fashion disclosed in Sierakowska and Shugar to form the desired mononucleotide-3'-phosphodiester, such as, for example, uridine-3'-(1-naphthyl) phosphate.

The synthesis schemes described by Sierakowska et al., and Rubsamen et al., suffer, however, from several major deficiencies. For example, in each synthesis method, the preparation of the key intermediate, 2',5'-bis-O-(tetrahydropyranyl)-uridine, involves an undesirable, lengthy chromotography. Further, the resulting product is a mixture of diastereomeric pairs in low yields; and this complicates subsequent synthetic steps. Finally, the overall synthesis is labor-intensive.

Closely similar schemes to those of Sierakowska et al. and Rubsamen et al. are disclosed in Polish Pat. No. 81969. In one synthesis described therein, 2',5'-di-O-tetrahydropyranyl-3'-uridine-(1-naphthyl) phosphate is formed in dicyclohexylcarbodiimide and pyridine by the reaction of a salt of 1-naphthylphosphoric acid, (e.g., the pyridine, aniline, lutidine or tri-n-buytlamine salt of the acid) with 2',5'-di-O-(tetrahydropyranyl)-uridine. In another synthesis described therein, uridine 2'-O-tetrahydropyranyl-5'-O-methyl-3'-(1-naphthyl) phosphate is formed in pyridine by the reaction of a salt of 1-naphthylphosphoric acid and 5'-O-methyl-2'-O-(tetrahydropyranyl)-uridine. These schemes likewise suffer from the deficiencies of the Sierakowska et al. and Rubsamen et al. methods.

In addition, methods are known for preparing oligoribonucleotides which incorporate the synthesis of 2',5'-diblocked nucleotides as intermediates. Thus, in J. Smrt and F. Sorm, Collection Czechoslav. Chem. Commun. 27, 73 (1962), uridylic acid is converted into 5'-O-acetyluridine 2',3'-cyclic phosphate which, after enzymatic cleavage of the cyclic phosphate by pancreatic ribonuclease, results in 5'-O-acetyluridine-3'-phosphate, which is then transformed into 2'-O-tetrahydropyranyl 5'-O-acetyluridine 3'-phosphate by the reaction with dihydropyran.

In this method, acetylation at the 5'-hydroxyl of the cyclic phosphate is utilized as a synthetic convenience for preparing intermediates in the synthesis of oligoribonucleotides. Deblocking of the 5'-acetyl is ultimately carried out in the formation of the desired oligoribonucleotide. This, however, does not describe a suitable method for synthesizing a chromogenic and/or fluorogenic mononucleotide-3'-phosphodiester. Moreover, insofar as is known, the Smrt et al. methods have not heretofore been utilized in making such chromogenic and/or fluorogenic mononucleotide-3'-phosphodiesters, despite the deficiencies of prior methods.

Thus, despite the considerable number of methods that have been developed and utilized for synthesizing various substrates suitable for use for monitoring enzymatic or catalytic activity, there remains the need for further development which can overcome the various shortcomings of the presently known synthetic methods. None of the synthesis schemes described above are currently being used commercially for the manufacture of mononucleotide-3'-phosphodiesters insofar as is known.

It is, accordingly, an object of the present invention to provide a novel method for synthesizing mononucleotide 3'-phosphodiesters having a chromogenic and/or fluorogenic functional group at the 3'-phosphate moiety of the furanoside ring. A related object is to provide a method for synthesizing such mononucleotides in a manner so as to eliminate the formation of undesirable diastereomeric pairs.

Another object is to provide a novel method for synthesizing chromogenic and/or fluorogenic mononucleotide 3'-phosphodiesters which is less labor intensive than previous syntheses.

Yet another object of this invention is to provide a novel synthesis of chromogenic and/or fluorogenic monucleotide 3'-phosphodiesters which results in improved overall yields.

Still another object of the present invention is to provide a novel synthesis of chromogenic and/or fluorogenic mononucleotide 3'-phosphodiesters, which may be carried out on a multigram scale sufficient for commercial use.

These and other objects and advantages of the present invention will become apparent from the following detailed description.

While the invention is susceptible to various modifications and alternative forms, there will herein be described in detail the preferred embodiments. It is to be understood, however, that it is not intended to limit the invention to the specific forms disclosed. On the contrary, it is intended to cover all modifications and alternative forms falling within the spirit and scope of the invention as expressed in the appended claims. For example, while the present invention will be primarily described in conjunction with the formation of a uridine-3'-phosphodiester, it should be appreciated that bases other than uracil may be employed, as will be described herein.

SUMMARY OF THE INVENTION

In general, the present invention is predicated on the discovery that mononucleotide-3'-phosphodiester substrates having a chromogenic and/or fluorogenic functional group at the 3'-phosphate moiety may be readily synthesized from a 2',5'-diblocked mononucleotide by reaction with a compound containing the desired chromogenic and/or fluorogenic moiety to form the 2',5'-blocked chromogenic and/or fluorogenic substrate. In general, a 2',3'-cyclic phosphate is first blocked at the 5'-hydroxyl to form an intermediate, which is subjected to enzyme cleavage of the 2'-ester bond thereby resulting in a 5'-blocked-3'-mononucleotide. The 5'-blocked-3'-mononucleotide is then reacted with a suitable blocking group to form a 2',5'-diblocked-3'-mononucleotide, which is in turn reacted with the desired chromophore and/or fluorophore to form the blocked substrate.

In accordance with an alternative procedure, the 2',5'-diblocked-3'-mononucleotide may be dephosphorylated to form the 2',5'-diblocked mononucleoside, which may then be reacted with a phosphorylated derivative of the desired chromophore and/or fluorophore.

The chromogenic and/or fluorogenic mononucleotide 3'-phosphodiester substrates may be utilized for monitoring the catalytic activity of a variety of enzymes, such as for example, ribonuclease A, T$_2$, and the like; and/or polypeptide pairs having the catalytic activity of such enzymes. The chromogenic and/or fluorogenic mononucleotide substrates formed by the method of this invention are especially useful in the immunoassay methodology disclosed in the previously identified co-pending Farina et al. application.

DETAILED DESCRIPTION OF THE PREFERRED EMBODIMENTS

In accordance with the method of the present invention, suitable starting materials comprise a mixture of the 2'- and 3'-phosphate isomers of a mononucleotide having the following structural formula:

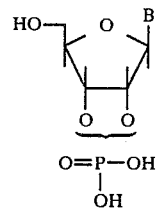

wherein B is a nucleotide base.

In this structure, there appear to be certain steric constraints which must be met in order to ultimately provide a substrate suitable for monitoring the catalytic activity of, for example, ribonuclease A-induced or related polypeptide pairs induced hydrolysis. Thus, the trans, cis orientation of the base B and substituents at positions 1'- and 2'-, 3'-, respectively, appear to have rigid structural constraints to provide a suitable substrate. However, the substituents at the 4'-position, that is, CH$_2$OH, may apparently have a configuration where the CH$_2$OH group is cis to both the 2'- and 3'- functional groups, without affecting the desirable attributes of the substrate. A. Holy and F. Sorn, *Biochemica. Biophysica. Acta.*, 161, 26 (1968). Accordingly, while the method of the present invention will be described in conjunction with the preparation of a substrate wherein the 4'-CH$_2$OH substituent is trans to the 2'-, 3'- substituents, it should be appreciated that the method is likewise equally applicable to the preparation of a substrate wherein the 4'-CH$_2$OH substituent is cis to the 2'-, 3'-substituents.

From the functional standpoint, the selection of the base should take into account the following factors, in addition to, of course, its effect on product stability: (1) any modulation (increase or decrease) of catalytic activity, (2) the difficulty of synthesis, (3) the effect on endogenous enzymatic activity and (4) the solubility in aqueous or other mediums of interest should not be adversely affected to any significant extent. Other factors to consider include possible effects on hydrolysis and non-specific medium induced hydrolysis.

A wide variety of pyrimidine analogs are useful bases, including uracil, dihydrouracil, cytosine, dihydrocytosine and halogenated uracils. Additionally, based on data extrapolated from results on the ribonuclease-induced hydrolysis of both the natural substrate, RNA, as well as various synthetic substrates, such as, for example, nucleotide homopolymers, F. M. Richards and W. W. Wyckoff in *The Enzymes*, (P. D. Boyer, Ed.), Academic Press, 3d Edition, Volume 4, pages 647–806, London and New York (1978), the following pyrimidine analogs should be suitable bases:

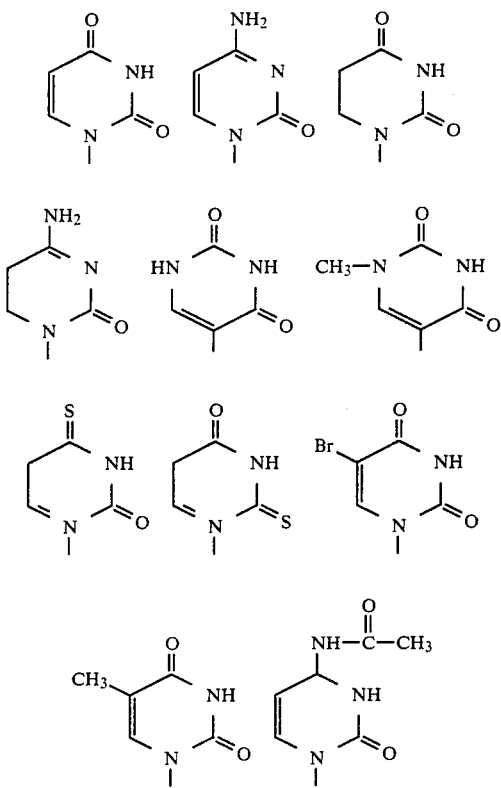

While the use of purine analogs as bases, such as, for example, adenosine and guanosine, will not provide active substrates for monitoring the catalytic activity of ribonuclease A, these bases should prove useful when ribonuclease $T_2$ activity is involved. Further, any other pyrimidine, purine or the like analogs may be used consistent with the functional considerations set forth herein.

In carrying out the first step of the method, the mixture of the 2'- and 3'- phosphate mononucleotide isomers are reacted with a condensation reagent to form a mononucleotide-2',3'-cyclic phosphate. A suitable condensation reagent is N, N'-dicyclohexylcarbodiimide (DCC). Other condensation reagents which may also prove useful include 1,1'-carbonyldiimidazole, 1-hydroxybenzotriazole monohydrate (HBT), 1-cyclohexyl-3-(2-morpholino-ethyl)-carbodiimide metho-p-toluenesulfonate (morpho-CDI), 1-(3-dimethylaminopropyl)-3-ethyl carbodiimide hydrochloride (EDC), N-ethoxycarbonyl-2-ethoxy-1, 2-dihydroquinoline, and ethyl 1,2-dihydro-2-ethoxy-1-quinoline carboxylate (EEDQ). The use of an auxiliary reagent such as tert-butyl alcohol may be helpful. Alternatively, N-hydroxy-succinimide, N-hydroxypiperidine, and N-hydroxyphthalimide may be perhaps employed in place of the tert-butyl alcohol.

The useful process parameters for carrying out the condensation step may vary over a wide range. With regard to the relative proportions of mononucleotide and condensation reagent, a mole ratio range of about 1:2 has been found suitable. Mole ratios of from about 1:1 to about 1:5, or perhaps more, should be likewise useful. A basic medium, provided by an ammonia solution, in a polar solvent such as N, N-dimethylformamide should be used. Other polar solvents such as pyridine, tetrahydrofuran and dioxane and reagents other than ammonia to provide the resulting basic medium should be capable of being used. The particular proportions of these components is not believed to be particularly critical, and suitable illustrative proportions are set forth in the Examples, as will be described hereinafter. The reaction can be carried out at a temperature of about 110° C. for a period of about 3 hours. A temperature range of about 30° C. to about 130° C. and a reaction time of about 1 to about 5 hours could be utilized.

The second step involves the formation of 5'-O-blocked uridine-2',3'-cyclic phosphate, formed from the reaction of uridine 2',3'-cyclic phosphate with a suitable blocking reagent. The reaction is set forth below:

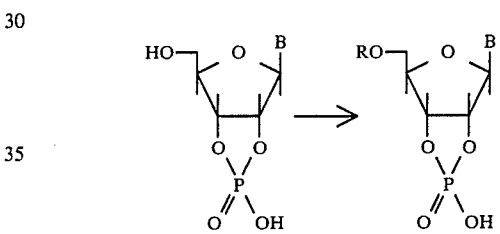

The blocking group and the manner in which blocking is effected should be selected so as to accomplish the following objectives: (1) the introduction of the blocking group should be capable of being readily carried out and should not adversely affect the integrity of the other important functional moieties, e.g., —avoidance of decyclization, (2) once introduced, the blocking group should be capable of being retained in subsequent synthetic steps until it is desired, if it is, to deblock and should further not interfere to any significant extent in such subsequent synthetic steps and (3) if retained, the blocking group should not adversely affect the performance of the resulting substrate in its intended application.

For example, if the blocking group is too large, it may decrease reactivity of the blocked mononucleotide in the phosphodiester synthetic step which will be described hereinafter. Further, if retained in the ultimate substrate, it may hinder the action of the enzyme or catalyst on the substrate. Functional groups which may in some fashion effect a modulation (i.e. —either increase or decrease) of the enzymatic or catalytic activity or which may interact with the phosphodiester substrate to destabilize it, as for example by hydrolysis, should be avoided. Other considerations include: (1) the solubility in aqueous or other mediums of interest should not be adversely affected to any significant extent, and (2) the effect on endogenous enzymatic activity, if the blocking group is retained.

In general, the blocking group R may be any acid or base labile moiety. Suitable blocking groups thus include alkyl, alkenyl, cycloalkyl, aryl, araalkyl, acyl, oxaalkyl, thioalkyl, oxacycloalkyl and thiocycloalkyl. More particularly, methyl, ethyl, allyl, cyclohexyl, phenyl, benzyl, nitrobenzyl, acetyl, 1-methoxyethyl, 1-ethoxyethyl, 1-ethylthioethyl, tetrahydropyranyl, tetrahydrothiofuranyl, tetrahydrothiopyranyl, and 4-methoxytetrahydropyran-4-yl may perhaps be suitably used.

Blocking of the 5'-hydroxyl substituent of the furanoside ring, as shown, where R is acetyl, is particularly advantageous due to elimination of the formation of undesirable diastereomeric pairs. In addition, the acetyl group is sufficiently small so that it does not decrease reactivity of the blocked mononucleotide in the phosphodiester synthetic step. Yet another advantage of the acetyl group as the 5'-blocking group is that overall yields of suitable substrate are significantly improved.

Further, with regard to performance considerations, the presence of the 5'-acetyl group in the final product does not appreciably affect the activity of the substrate towards various enzymes, such as, for example, ribonuclease A or T₂ or catalytic polypeptide pairs, such as, for example, the S-peptide/S-protein polypeptide pair utilized in the methodology described in the co-pending Farina et al. application. Also, its presence does not adversely affect the stability of the resulting substrate. For these two reasons, it is unnecessary to remove the acetyl group. Indeed, the presence of the acetyl group in the resulting substrate as the 5'-blocking group may well minimize or obviate various deleterious effects such as, for example, non-specific, medium-induced hydrolysis which could possibly occur in a deblocked substrate.

The blocking of the 5'-hydroxyl of the 2', 3'-cyclic phosphate can be suitably carried out in an aprotic polar solvent such as those which have been previously described. When an acetyl group is used for blocking, the reaction may be carried out using the following parameters: (1) a concentration of the unblocked product in pyridine of from about 0.2M to about 0.5M, (2) acetic anhydride in stoichiometric excess of the unblocked product of from about 60 to about 80 equivalents, (3) a temperature of from about 15° C. to about 30° C. and (4) a reaction time of from about 5 to about 15 hours. These parameters may be widely varied, and the following should likewise be useful: (1) a concentration of from about 0.1 to about 1.0M, (2) use of acetic anhydride or other acetylation reagents such as acetyl chloride or other acetyl halides in excess of from about 10 to about 100 equivalents, (3) temperatures of from about 10° C. to about 50° C. and (4) a reaction time of from about 2 to about 20 hours. Other blocking groups such as alkyl, cycloalkyl and araalkyl may be introduced by known displacement reactions. Introduction of oxaalkyls, oxacycloalkyls, thioalkyl and thiocycloalkyls may be carried out by acid-catalyzed addition to the corresponding olefinic ethers; and this will be more fully described in the discussion of the 2'-blocking group which follows.

The third step of the synthesis involves the specific phosphate ring opening to provide a specific 3'-phosphate moiety to which a suitable chromophore and/or fluorophore may be chemically bonded. The reaction requires a specific and efficient catalyst so that essentially only the 3'-uridine phosphate is formed. A suitable catalyst for this purpose is pancreatic ribonuclease.

Other synthetic or natural catalysts having the requirements defined herein may likewise be used. The reaction sequence is depicted below:

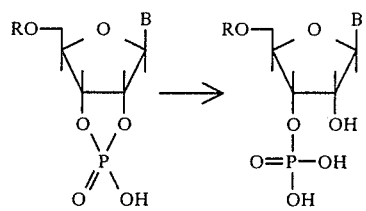

The reaction may be carried out in an aqueous polar solvent (e.g., —pyridine) solution containing, for example, about 20% pyridine, using a sufficient amount of catalyst to provide convenient reaction times. As an example, a catalyst concentration of about 1% by weight, based on the weight of the cyclic phosphate, is satisfactory.

The resulting decyclized product must then be isolated by removal of the catalyst and concentration of the liquid product. This may be accomplished by, for example, removing the catalyst using an ion exchange column and then concentrating the reaction solution. When pyridine has been used, the resulting product is a pyridinium salt. If desired, the concentrated pyridinium salt may be converted to ammonium, tert-butyl ammonium, calcium, sodium, lithium or the like salt. This may be carried out by precipitation from an appropriate aqueous solution (e.g., —aqueous tetrahydrofuran). The use of the ammonium salt offers a particular benefit in that modification is unnecessary in subsequent synthetic steps. On the other hand, the calcium salt provides a more crystalline, readily isolated and easier product to handle.

The fourth step of this procedure involves blocking of the 2'-hydroxyl group:

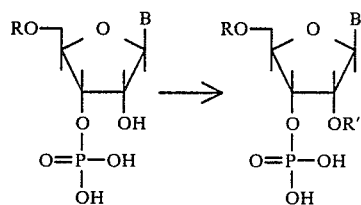

wherein R' is a 2'-O-blocking group.

Suitable 2'- blocking groups should meet the following criteria: (1) readily introduced without affecting the other key functionalities, (2) compatible with the subsequent phosphodiester formation step, and more particularly, should minimize or eliminate undesired side reactions in such step, (3) sufficiently stable to allow long-term storage without any adverse deleterious affects and (4) easily removed without disruption of the phosphodiester bond. These criteria, and especially the last one, are most readily met by use of a blocking group capable of being introduced and removed by acid-catalyzed reactions. Thus, suitable blocking groups include oxaalkyl, thioalkyl, oxacycloalkyl, silyl derivatives and thiocycloalkyl. More particularly, tetrahydropyranyl, 4-methoxytetrahydropyran-4-yl, and tert-butyldimethylsilyl may be used.

The blocking reaction may be accomplished in an aprotic polar solvent, such as N, N-dimethylformamide or dioxane. Diglyme, tetrahydrofuran or acetone may also be used. As a specific example, when the blocking group is tetrahydropyranyl, blocking can be carried out by combining dihydropyran or 4-methoxy-5, 6-dihydro-2-H-pyran, generally in an amount well in excess of the stoichiometric amount to insure that the reaction goes to completion in a convenient time period, with a catalytic amount of an acid catalyst such as dry hydrogen chloride in dioxane. The reaction will generally be completed in about 2 to about 15 hours. The temperature may be varied from about −20° C. to about 25° C. Other useful, acid catalysts include p-toluenesulfonic acid and trifluoroacetic acid. Likewise, the reaction time may be as little as one hour or as long as 20 hours, and the temperature can vary from about −30° C. to about 50° C. This general reaction scheme is equally applicable for introducing the other blocking groups set forth herein by an acid-catalyzed reaction. Alternatively, a blocking group may be used which is capable of being introduced by known displacement reactions and removed by photochemical means. An example of this type of blocking group is o-nitrobenzyl.

In one embodiment of this invention, the fifth step forms the chomogenic and/or fluorogenic mononucleotide-3'-phosphodiester substrate by the esterification reaction of the intermediate 2',5'-O-diblocked mononucleotide with a fluorophore or chromophore moiety R". The reaction is depicted below:

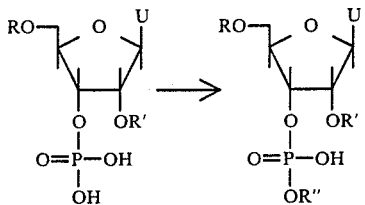

Functionally, R" can be defined as any moiety which will provide the substrate with fluorogenic and/or chromogenic properties. The R" group may be an aryl, araalkyl, heteroaryl or heterocyclic compound. In the preferred embodiment, R" is umbelliferonyl, 4-methylumbelliferonyl or 3-flavonyl. Other suitable R" groups include aryls such as, for example, 1-naphthyl. Further other R groups which are suitable are aryl groups which incorporate electron withdrawing and conjugating substituents which increase the acidity of ortho and para benzoic acids. Such groups include, ortho, meta and para nitrophenyl, 2,4-dinitrophenyl, cyanophenyl, acylphenyl, carboxyphenyl, phenylsulfonate phenylsulfonyl and phenylsulfoxide. In general, mixtures of mono and bi-substituted derivatives may likewise be suitable.

The alcohol form of the chromophore and/or fluorophore moiety is typically, and preferably, used to form the blocked substrate product.

The esterification reagent selected should not cause deblocking of the 2'-blocking group, and should be easily separated from the phosphodiester formed. Further, and importantly, the reagent selected should provide high yields under mild reaction conditions. Suitable reagents include 2,4,6-triisopropylbenzenesulfonyl chloride, N,N'-dicyclohexylcarbodiimide and mesitylenesulfonyl chloride, toluenesulfonyl chloride, mesitylenesulfonyl imidazolide, p-toluenesulfonyl imidazolide, picryl chloride, 1-(3-dimethylamino-propyl)-3-ethyl carbodiimide hydrochloride, and other carbodiimide analogs with or without additives such as, N-hydroxy-succinimide, N-hydroxyphthalimide, and the like are also suitable.

With respect to the 2',5'-diblocked-uridine-3'-monophosphate, it has been found necessary under the reaction conditions employed to use either the pyridinium or the ammonium salts. Accordingly, if the calcium or the metallic ion salts have been utilized in the prior synthetic steps, it has been found necessary to convert to the desired salts by ion exchange.

With regard to the esterification reaction conditions, an excess of the chromogenic and/or fluorogenic alcohol is used to maximize yield, although an excess is not required. To maximize the yield, it has been found satisfactory to use a molar ratio of about 2:1. The reaction may be carried out in an aprotic polar solvent such as N,N-dimethylformamide, dioxane or tetrahydrofuran and the like, in the presence of a base, such as, pyridine. It has been found suitable to employ dry pyridine base as a solvent, at a temperature in the range of from about −20° C. to about 25° C. Further, the time for the reaction may range from about 5 to 18 hours. These reaction conditions may be varied, if desired. Thus, the temperature may range from about −20° C. to about 50° C. and the time from 2 to 72 hours.

An important aspect of this method of synthesis is that it provides a substrate suitable for use in, for example, immunoassays, without requiring purification by, for example, chromatography, prior to such use.

In an alternative embodiment of the present invention, the fifth step of the procedure provides first for the formation of a 2',5'-diblocked mononucleoside, by dephosphorylation of the 2',5'-diblocked mononucleotide by the utilization of methods known in the art, such as, by the use of, for example, phosphatase or Pb(II) hydroxide, to effect cleavage of the 3'-phosphate. The 2',5'-diblocked mononucleoside so formed may then be reacted with a phosphorylated derivative of the desired chromophore and/or fluorophore moiety, to form the 2',5'-diblocked mononucleotide-3'-phosphodiester substrate. The chromophore and/or fluorophore moieties, R", suitable for use in this embodiment of the invention are the same as the R" moieties previously described.

The selection of the particular embodiment used to form the phosphodiester may depend on the particular chromophore and/or fluorophore moiety used. For example, with the naphthyl chromophore, it may well be desirable to utilize the alternative embodiment.

The 2',5'-diblocked substrate prepared by either of the alternative methods, is a stable compound which may be stored for extended periods. However, deblocking of the 2'-blocking group is necessary to provide a suitable enzyme substrate. The deblocking reaction is set forth as follows:

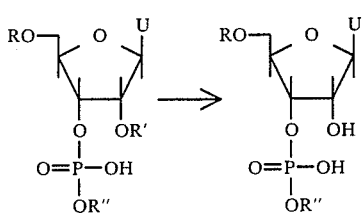

Acid-catalyzed deblocking may be carried out in a protic solvent such as water using mild conditions with dilute acid for a short period of time. Commonly used acid catalysts include hydrochloric acid, trifluoroacetic acid, p-toluenesulfonic acid, and acetic acid. A preferred reagent is dilute hydrochloric acid in a molar concentration of from about 0.01 to about 1, more usually 0.01 to 0.1 and preferably 0.01 to 0.05. Acid forms of ion exchange resins may also be used. When the blocking group is silyl, deblocking may be effected by a nucleophilic reagent such as, for example, tetrabutylammonium fluoride.

With regard to the deblocking conditions, ambient temperatures are suitable. The deblocking reaction time may be varied over a relatively wide period, depending on the concentration of the deblocking reagent and the temperature at which the deblocking reaction is carried out. Generally, the higher the temperature and the higher the concentration of acid, the shorter will be the appropriate reaction period. Thus, the reaction may be carried out for from about 5 minutes to about 24 hours, more usually from about 10 minutes to about 120 minutes, and preferably from about 20 to about 60 minutes. The use of too severe reaction conditions should be avoided as this may lead to deleterious hydrolysis of the deblocked substrate.

The following Examples are merely illustrative of the present invention and are not intended as a limitations on the scope thereof.

EXAMPLE I

This Example illustrates the preparation of uridine 2',3'-cyclic phosphate.

A solution of 10 g, 0.031 mole, comprising a mixture of uridine 2'- and 3'-phosphates in 74 ml of 3N-ammonia was successively mixed with 60 ml of N,N-dimethylformamide (DMF), and a solution of 15 g, 0.075 mole, of dicyclohexylcarbodiimide in 60 ml of tert-butyl alcohol. The resulting reaction mixture was refluxed for three hours in an oil bath at 120° C.

A high pressure liquid chromotography (HPLC) analysis was done on a portion of the reaction mixture to determine whether the starting materials were converted to product. Aliquots of the reaction product mixture were concentrated under vacuum (bath 35° C.), the residue was dissolved in water, and the solution was filtered through a 5 μm Millipore ® filter. Samples were then injected into a Whatman Partisil ® 10/25 SAC column and eluted with buffer composed of 20% phosphate, 0.05M at about pH 6.25, and 80% water at a flow rate of 1 ml/min. The HPLC analysis showed a quantitative conversion of starting uridine into product.

The total product mixture was then allowed to cool to room temperature, and dicyclohexylurea precipitate was separated by filtration and washed with 20 ml of DMF. The filtrate was then evaporated in vacuo at 12-15 Torr, bath at about 35° C., and the residue was shaken with 100 ml of water and filtered to remove dicyclohexylurea. The solid was washed further with 20 ml of water, and combined solutions were extracted twice with 150 ml of ether, and evaporated to dryness in vacuo, bath at about 35° C. The residue was co-evaporated with two 100 ml portions of pyridine, using a liquid nitrogen trap at 0.01 Torr to obtain a glassy product, uridine 2',3'-cyclic phosphate.

EXAMPLE II

This Example illustrates the preparation of 5'-O-acetyluridine 2',3'-cyclic phosphate.

The uridine 2',3'-cyclic phosphate, prepared in Example I was dissolved in 100 ml of anhydrous pyridine and 200 ml of acetic anhydride. The solution was kept in the dark at room temperature overnight. At this point, an aliquot of the reaction product was analyzed by HPLC at the conditions given in Example I. The HPLC showed one major peak at 1.7 minutes, which is indicative of the product 5'-O-acetyluridine 2',3'-cyclic phosphate. The total product mixture was evaporated to dryness at 0.1-1 Torr bath at about 35° C., using a liquid nitrogen trap. The residue was co-evaporated with two 50 ml portions of pyridine to remove residual acetic anhydride, and then dissolved in 100 ml of 50% aqueous pyridine. After stirring for one hour at room temperature, the solution was evaporated to dryness at room temperature, at 0.05 Torr, to obtain product, 5'-O-acetyluridine 2',3'-cyclic phosphate.

EXAMPLE III

This Example illustrates the preparation of the pyridinium of 5'-O-acetyluridine 3'-phosphate.

The glassy product, 5'-O-acetyluridine 2',3'-cylic phosphate prepared in Example II was dissolved in 200 ml of 20% aqueous pyridine. To the solution was added 50 mg of pancreatic ribonuclease in 5 ml of water. The mixture was kept at room temperature overnight for approximately 15 hours with stirring in the dark. At this point an aliquot of the reaction product was analyzed by HPLC at the conditions given in Example I. The HPLC showed one major peak at 4.5 minutes, which is indicative of the product 5'-O'acetyluridine 3'-phosphate. The product mixture was then passed through a 2.2×4 cm ion exchange resin column of Dowex ® 50W-X8, in which 100-200 mesh, hydrogen ion form resin had been converted to the pyridinium form before use. The resin was eluted with 300 ml of 20% aqueous pyridine. The eluant solution was concentrated to an oily residue at 0.1-1 Torr, at about 35° C. The oily residue was dissolved in 5 ml of water and 200 ml of tetrahydrofuran (THF). To the solution was added 27% $NH_4OH$ dropwise with stirring until no more precipitate formed. Approximately 3 ml $NH_4OH$ was added. The mixture was kept cold overnight, filtered, and the residue was co-evaporated twice with some dimethylformamide. The resulting residue contained the pyridinium salt of 5'-O-acetyluridine-3'-phosphate.

EXAMPLE IV

This Example illustrates the preparation of 5'-O-acetyl-2'-O-(tetrahydropyran-2-yl)uridine 3'-pyridinium phosphate.

A stirred suspension of 12 g, 0.026 mole, of the finely-ground pyridinium salt of 5'-O-acetyluridine-3'-phosphate prepared in Example III, 160 ml of anhydrous N,N-dimethylformamide, and 70 ml of dihydropyran, was cooled to −20° C., and treated dropwise with 14.2 ml of 5M hydrogen chloride in dioxane over a 15 minute period, under exclusion of atmospheric moisture. The cooling bath was then removed and stirring was continued until a clear solution was obtained, i.e., about two hours. After storage overnight at room temperature, the mixture was cooled to −20° C. and treated with 12 ml of triethylmine and 3 ml of ammonium hydroxide; and the resulting suspension was poured into 500 ml of THF and 500 ml of ether. The precipitate was collected and removed on a medium porosity sintered-glass funnel. The filtrate was evaporated under vacuum to evaporate solvent and unreacted dehydropyran. The residue was taken into 50 ml tetrahydrofuran and stirred. To the suspension was added 100 ml ether to separate the product from tetrahydrofuran polymer. The ether layer was separated and washed one more time with 50 ml ether. The residue was dried in aspirator vacuum and then in high vacuum using a liquid nitrogen trap and the pyridinium salt product was obtained.

EXAMPLE V

This Example illustrates the preparation of 5'-O-acetyl-2'-O-(tetrahydropyran-2-yl)uridine 3'-(4-methylumbelliferone-7-yl) pyridinium phosphate.

A mixture comprising 1.00 g (2.01 mmole) of the 5'-O-acetyl-2'-O-(tetrahydropyran-2-yl)uridine pyridinium phosphate prepared in Example IV and 0.531 g (3.00 mmole) of 4-methylumbelliferone and 1.52 g, (5.02 mmole) of 2,4,6-triisopropylbenzenesulfonyl chloride, in 6 ml of dry pyridine, was stirred under exclusion of atmospheric moisture. The mixture gradually became a homogeneous yellow solution after about 30 minutes at room temperature. After about one hour, the pyridine HCl salt precipitated. After stirring overnight, 6 ml of water were added and the stirring was continued for an additional two hours. The mixture was concentrated at room temperature, in vacuo, using a liquid nitrogen trap, and the solid product mixture was dissolved in 15 ml of water. The solution was extracted five times with 50 ml ether, per extraction, until most of the unreacted 4-methylumbelliferone was removed, as indicated by the decrease in fluroscent emission at 450 nm when the solution was excited at 325 nm. The water solution was lyophilized, in vacuo, to give product containing 5'-O-acetyl-2'-O-(tetrahydropyran-2-yl)-uridine-3'-(4-methylumbelliferone-7-yl) pyridinium phosphate.

EXAMPLE VI

This Example illustrates the preparation of 5'-O-acetyluridin-3'-(4-methylumbelliferone-7-yl) pyridinium phosphate.

Prior to use, the 5'-O-acetyl-2'-O-(tetrahydropyran-2-yl)-uridine-3'-(4-methylumbelliferone-7-yl) pyridinium phosphate prepared in Example V was readily deblocked with hydrochloric acid. Fifteen milligrams of the 2',5'-diblocked phosphodiester were added to 1 ml of 0.01N HCl to give a clear solution. After 45 minutes, the product solution was extracted six times with 1 ml of ether to remove residual 4-methylumbelliferone. Nitrogen was then blown across the aqueous solution to remove the last traces of ether. The working solution was prepared by diluting to 100 ml with 0.1N sodium acetate buffer of about pH 5.0. The substrate was stable in the working buffer for at least two days at 4° C.

EXAMPLE VII

This Example illustrates the preparation of the calcium salt of 5'-O-acetyluridine 3'-phosphate.

The 5'-O-acetyluridine-2',3'-cylic phosphate prepared as described in Examples I and II (using 4 grams of a mixture of the 2'- and 3'- phosphate isomers of uridine) was dissolved in 100 ml of 20% aqueous pyridine. To the solution there was added 50 mg of pancreatic ribonuclease A. The solution was stirred in the dark at room temperature for 15 hours.

An aliquot of the solution was analyzed, after removal of ribonuclease A by passing through Dowex ®-50 column, by HPLC at the conditions given in Example I. The analysis showed a very small starting amount of cyclic phosphate at 1.7 minutes and a major product peak at 4.5 minutes.

An additional 20 mg of ribonuclease A was added to the remaining product mixture and the mixture was allowed to stir at room temperature for an additional 3 hours. The product solution was passed through a Dowex ®-50 (1×5 cm) column by eluting with 160 ml of 20% aqueous pyridine. The solution was concentrated to about 50 ml and poured into 1000 ml of anhydrous ethanol containing 5 g of calcium chloride. The mixture was stirred at room temperature for 2 hours and then allowed to stand to precipitate the calcium salt. The precipitate was collected by centrifugation at 3000 rpm for about 5 to 10 minutes, and repeated washing (7×150 ml) with ethanol and centrifugation.

The calcium salt cake was washed with two 150 ml portions of ether and dried in air. After drying further in vacuo, there was obtained 13.1 g of product containing the calcium salt of 5'-O-acetyluridine 3'-phosphate as confirmed by HPLC analysis (at the conditions given above) which showed one major product peak at 4.5 minutes.

EXAMPLE VIII

This Example illustrates the preparation of 5'-O-acetyl-2'-0-(4-methoxytetrahydropyran-4-yl)uridine 3'-calcium phosphate, utilizing 5,6-dihydro-4-methoxy-2H-pyran as a 2'-blocking reagent.

One gram of 5'-O-acetyluridine 3'-calcium phosphate prepared in Example VII was dissolved in 8 ml of dry N,N-dimethylformamide. To this solution was added 5.0 g of 5,6-dihydro-4-methoxy-2H-pyran. The solution was cooled in an acetone-ice bath to below 0° C. To the stirred mixture there were added 1.4 ml of 5M hydrogen chloride in N,N-dimethylformamide dropwise in a moisture-excluded atmosphere. After about 20 minutes, the cooling bath was removed and the reaction mixture was stirred at room temperature overnight, about 15 hours. This mixture was again cooled in an acetone-ice bath, and 25 ml of triethylamine was added dropwise with stirring. The product mixture was poured into 100 ml of ether and filtered to collect white powder. The powder was washed with 100 ml of ether, and with 100 ml of 1% triethylamine in chloroform.

The solid was first air dried and then further dried in vacuo to give 1.398 g of product containing 5'-O-acetyl-2'-0-(4-methoxytetrahydropyran-4-yl)uridine 3'-calcium phosphate.

HPLC on Whatman Partisil ® PXS 10/25 SAX column eluting with 0.01M phosphate buffer, pH 6.3, flow rate 1 ml/min., UV detection at 253 nm, showed product at 3.4 min., while the starting materal has retention time of 4.7 minutes.

EXAMPLE IX

This Example illustrates the preparation of 5'-O-acetyl-2'-O-(4-methoxytetrahydropyran-4-yl)uridine-3'-(4-methylumbelliferone-7-yl) phosphate.

The hydrogen ion form of Bio-Rad AG ® 50W-X8 cation exchange resin, 1.1 g, was converted into the pyridinium form. To the column there was added 100 mg of the product containing 5'-O-acetyl-2'-O-(4-methoxytetrahydropyran-4-yl)uridine 3'-calcium phosphate prepared in Example VIII dissolved in cold 50% pyridine solution, and the column was eluted with 270 ml of 50% pyridine solution. The eluant solution was collected in a flask cooled in an ice-water bath. The eluant solution was concentrated to 15 ml on a rotary evaporator using a dry ice trap at bath temperature of about 25° C. The remaining solution was further concentrated in vacuo using a liquid nitrogen trap (0.05 mm Hg) at room temperature to obtain a glassy residue. The residue was further dried by evaporating twice with dry pyridine.

Finally, the residue was dissolved in 1 ml of dry pyridine and the mixture was charged with 52.72 mg of 4-methylumbelliferone and 102.7 mg of 2,4,6-triisopropylbenzenesulfonyl chloride. The mixture was cooled in an ice-water bath with stirring for 15 minutes. The resulting yellow solution was further stirred at room temperature for 2 hours and allowed to stir overnight, that is, about 15 hours at about 4° to 8° C. The total product mixture was then stirred with 3 ml of a saturated solution of tetraethylammonium bromide for 5 minutes, and then extracted five times with chloroform. The chloroform layer was concentrated in vacuo to yield 635 mg of light gray solid crude product.

The phosphodiester was further purified by an anion exchange column chromatography eluted with ammonium bicarbonate buffer. The appropriate fractions were identified by assay with RNase after deblocking in the manner given in Example V. The fractions so identified were pooled and concentrated to give 137 mg of solid, which was then dissolved in methanol and evaporated repeatedly in vacuo to remove ammonium bicarbonate. As a result, 59 mg of product containing 5'-O-acetyl-2'-O-(4-methoxytetrahydropyran-4-yl)-uridine-3'-(4-methylumbelliferone-7-yl) phosphate were obtained.

EXAMPLE X

This Example illustrates the preparation of 5'-O-acetyl-2'-O-(4-methoxytetrahydropyran-4-yl)uridine-3'-flavonyl phosphate.

Fifty milligrams of the product containing 2'-O-(4-methoxytetrahydropyran-4-yl)-5'-O-acetyl-3'-uridine calcium phosphate prepared in Example VIII, was converted into the pyridinium salt by passing it through a pyridinium form of Bio-Rad AG ® 50W-X8, cation exchange column. The pyridine solution was concentrated in vacuo and further dried by repeated evaporation with dry pyridine to obtain a glassy residue.

The glassy residue was dissolved in 1 ml of dry pyridine, and the solution was charged with 35.6 mg of 3-hydroxyflavone and 51.4 mg of 2,4,6-triisopropylbenzenesulfonyl chloride, with stirring in an ice-water bath under nitrogen atmosphere. After 15 minutes, the mixture was allowed to warm up to room temperature and stirred over the weekend, about 3 days.

The reaction mixture was then monitored for product formation. A 0.3 ml aliquot of the reaction mixture was stirred with 1 ml of saturated tetraethylammonium bromide and extracted with chloroform 4 times. The chloroform was evaporated, and the resulting yellow solid was treated with 0.01N HCl for 40 minutes. The solution was then buffered at pH 5 with a 0.1M acetate buffer containing $4 \times 10^{-3}$ aluminium chloride and 1% dimethylsulfoxide. The resulting buffered solution, in the presence of RNase $T_2$ enzyme, produced fluorescent emission characteristics of aluminum chelated 3-hydroxyflavone, thereby indicating that the desired product had formed.

The remainder of the reaction mixture was stirred for 5 minutes with 2 ml of a saturated solution of tetraethylammonium bromide. The mixture was then extracted four times with chloroform. The chloroform layer was dried over anhydrous sodium sulfate and concentrated to give 0.355 g of yellow solid product. The product was further purified by chromatography on a silica gel column, $2.5 \times 6.5$ cm, and eluted with 10% methanol in chloroform. Fractions of 100 milliliters each were collected and fractions 9, 10 and 11 were shown to have positive substrate activity when deblocked in acid, and assayed with RNase.

The fractions 9, 10 and 11 were combined and concentrated to obtain 160 mg of product containing 5'-O-acetyl-2'-O-(4-methoxytetrahydropyran-4-yl)-uridine-3'-flavonyl phosphate.

What is claimed is:

1. A method for preparing a substrate capable of undergoing catalytic-induced hydrolysis of the phosphate ester at the 3'-position to yield a species capable of being monitored spectrophotometrically or fluorometrically, comprising
   (a) forming a mononucleotide 2',3'-cylic phosphate of the formula

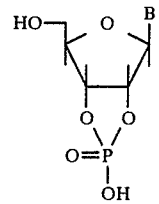

wherein B is a nucleotide base, and wherein the CH$_2$OH group at the 4'-position is either cis or trans to the cyclic phosphate, by reacting a mixture of 2'- and 3'-phosphate mononucleotide isomers with a condensation reagent;
   (b) reacting said mononucleotide 2',3'-cyclic phosphate with a 5'-blocking reagent to form a mononucleotide 5'-O-blocked-2',3'-cyclic phosphate of the formula

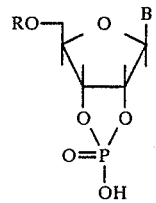

wherein R is selected from the group consisting of alkyl, alkenyl, cycloalkyl, aryl, araalkyl, acyl, oxaalkyl, thioalkyl, oxacycloalkyl and thiocycloalkyl;
   (c) opening the phosphate ring of said mononucleotide 5'-O-blocked-2',3'-cyclic phosphate by reaction thereof with a suitable catalyst so that essentially only a mononucleotide 5'-O-blocked 2'-hydroxyl 3'-phosphate of the formula

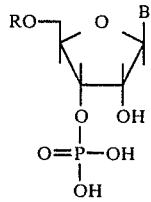

is formed;

(d) reacting said mononucleotide 5'-O-blocked 2'-hydroxyl 3'-phosphate with a 2'-O-blocking reagent to form a mononucleotide 2'-O-blocked-5'-O-blocked-3'-phosphate of the formula

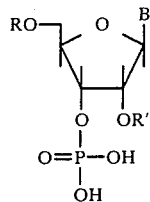

wherein R' is selected from the group consisting of oxaalkyl, thioalkyl, oxacycloalkyl, silyl derivatives and thiocycloalkyl; and (e) esterifying said mononucleotide 2'-O-blocked-5'-O-blocked-3'-phosphate with a chromophore or fluorophore to form a mononucleotide 2'-O-blocked-5'-O-blocked phosphodiester of the formula

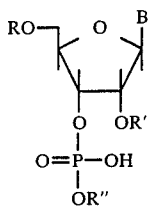

wherein R" is selected from the group consisting of a chromophore or fluorophore moiety;

said 2'-blocking member being capable of at least essentially blocking medium-induced hydrolysis of the phosphate ester at the 3'-position, and said 2'-blocking member being capable of being removed to provide a substrate characterized by the ability to undergo catalytic-induced hydrolysis of the phosphate ester at the 3'-position to yield a species capable of being monitored spectrophotometrically or fluorometrically.

2. A method for preparing a substrate capable of undergoing catalytic-induced hydrolysis of the phosphate ester at the 3'-position to yield a species capable of being monitored spectrophotometrically or fluorometrically, comprising (a) forming a mononucleotide 2',3'-cyclic phosphate of the formula

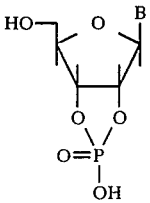

wherein B is a nucleotide base, and wherein the CH₂OH group at the 4'-position is either cis or trans to the cyclic phosphate, by reacting a mixture of 2'- and 3'-phosphate mononucleotide isomers with a condensation reagent;

(b) reacting said mononucleotide 2',3'-cyclic phosphate with a 5'-blocking reagent to form a mononucleotide 5'-O-blocked-2',3'-cyclic phosphate of the formula

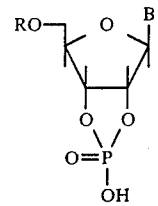

wherein R is selected from the group consisting of alkyl, alkenyl, cycloalkyl, aryl, araalkyl, acyl, oxaalkyl, thioalkyl, oxacycloalkyl, and thiocycloalkyl;

(c) opening the phosphate ring of said mononucleotide 5'-O-blocked-2-,3'-cyclic phosphate by reacting thereof with a suitable catalyst so that essentially only a mononucleotide 5'-O-blocked 2'-hydroxyl 3'-phosphate of the formula

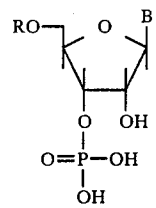

is formed;

(d) reacting said mononucleotide 5'-O-blocked-2'-hydroxyl 3'-phosphate with a 2'-O-blocking reagent to form a mononucleotide 2'-O-blocked-5'-O-blocked-3'-phosphate of the formula

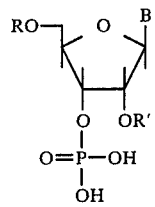

wherein R' is selected from the group consisting of oxaalkyl, thioalkyl, oxacycloalkyl, silyl derivatives and thiocycloalkyl; and (e) reacting said mononucleotide 2'-O-blocked-5-O-blocked-3'-phosphate with a dephosphorylating agent to cleave the 3'-phosphate to form a 2',5'-diblocked mononucleotide and reacting said 2,5-diblocked mononucleotide with a phosphorylated derivative of a chromophore or fluorophore to form a mononucleotide 2'-O-blocked-5'-O-blocked phosphodiester of the formula

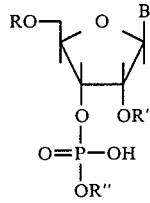

wherein R" is selected from the group consisting of a chromophore or fluorophore moiety;

said 2'-blocking member being capable of at least essentially blocking medium-induced hydrolysis of the phosphate ester at the 3'-position, and said 2'-blocking member being capable of being removed to provide a substrate characterized by the ability to undergo catalytic-induced hydrolysis of the phosphate ester at the 3'-position to yield a species capable of being monitored spectrophotometrically or fluorometrically.

3. The method of claim 2 comprising the further step of reacting said mononucleotide 2'-O-blocked-5'-O-blocked phosphodiester with a deblocking agent to remove said 2'-blocking member to provide an enzyme substrate of the formula

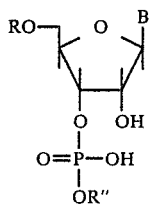

wherein said substrate is characterized by the ability to undergo catalytic-induced hydrolysis of said phosphodiester to yield a species capable of being monitored spectrophotometrically or fluorometrically.

4. The method of claim 1 comprising the further step of reacting said mononucleotide 2'-O-blocked-5'-O-blocked phosphodiester with a deblocking agent to remove the 2'-blocking member to provide an enzyme substrate of the formula

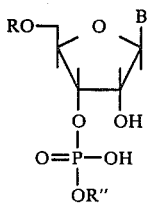

wherein said substrate is characterized by the ability to undergo catalytic-induced hydrolysis of said phosphodiester to yield a species capable of being monitored spectrophotometrically or fluorometrically.

5. The method of claim 1 wherein said base is a pyrimidine analog.

6. The method of claim 1 wherein said base is a purine analog.

7. The method of claim 1 wherein said base is a member selected from the group consisting of uracil, dihydrouracil, cytosine, dihydrocytosine and halogenated uracils.

8. A method of claim 1 wherein said base is uracil.

9. The method of claim 1 wherein said R is selected from the group consisting of methyl, ethyl, allyl, cyclohexyl, phenyl, benzyl, nitrobenzyl, acetyl, 1-methoxyethyl, 1-ethoxyethyl, 1-ethylthioethyl, tetrahydropyranyl, tetrahydrothiofuranyl, tetrahydrothiopyranyl, and 4-methoxytetrahydropyran-4-yl.

10. The method of claim 9 wherein R is acetyl.

11. The method of claim 1 wherein R' is selected from the group consisting of tetrahydropyranyl, 4-methoxytetrahydropyran-4-yl, and tert-butyldimethylsilyl.

12. The method of claim 11 wherein R' is tetrahydropyranyl.

13. The method of claim 11 wherein R' is 4-methoxytetrahydropyran-4-yl.

14. The method of claim 1 wherein said moiety is a member selected from the group consisting of aryl, araalkyl, heteroaryl or heterocyclic compound.

15. The method of claim 4 wherein said moiety is a member selected from the group consisting of umbelliferonyl, 4-methylumbelliferonyl, 3-flavonyl, 1-napthyl, o-nitrophenyl, m-nitrophenyl, p-nitrophenyl, 2,4-dinitrophenyl, cyanophenyl, acylphenyl, carboxyphenyl, phenylsulfonate, phenylsulfonyl and phenylsulfoxide.

16. The method of claim 15 wherein said moiety is 1-napthyl.

17. The method of claim 15 wherein said moiety is 4-methylumbelliferonyl.

18. The method of claim 15 wherein said moiety is 3-flavonyl.

19. The method of claim 1 wherein said 2'-O-blocked-5'-O-blocked phosphodiester is formed by an esterification reaction of said 2'-O-blocked-5'-O-blocked-2'-phosphate with an alcohol form of said moiety.

20. The method of claim 19 wherein said esterification reaction is carried out in the presence of an esterification reagent selected from the group consisting of 2,4,6,-triisopropylbenzenesulfonyl chloride, N, N'-dicyclohexylcarbondimide, mesitylenesulfonyl chloride, toluenesulfonylchloride, mesitylenesulfonyl imidazole, p-toluenesulfonyl imidazole, picryl chloride and 1-(3-dimethylaminopropyl)-3-ethyl carbodiimide hydrochloride.

21. The method of claim 20 wherein said esterification reaction is carried out in the presence of an additive selected from the group consisting of N-hydroxysuccinimide and N-hydroxyphthalimide.

22. The method of claim 20 wherein said esterification reaction is carried out in the presence of pyridine.

23. The method of claim 22 wherein said esterification reaction is carried out at a temperature in the range of from about $-20°$ C. to about $25°$ C.

24. The method of claim 23 wherein said esterification reaction is carried out for a time of from about 5 to about 18 hours.

25. The method of claim 4 wherein said removal of said 2'-blocking member is carried out in a protic solvent.

26. The method of claim 25 wherein said protic solvent is water.

27. The method of claim 26 wherein said removal of said 2'-blocking member is carried out in the presence of an acid selected from the group consisting of hydrochloric acid, trifluoroacetic acid and p-toluenesulfonic acid.

28. The method of claim 27 wherein said acid is hydrochloric acid in a molar concentration of from about 0.01 to about 1.

29. The method of claim 28 wherein the molar concentration of hydrochloric acid is from about 0.01 to 0.05.

30. The method of claim 29 wherein the reaction is carried out at ambient temperature.

31. The method of claim 30 wherein the reaction is carried out for from about 5 minutes to about 24 hours.

* * * * *